(12) United States Patent
Osadchy et al.

(10) Patent No.: US 6,266,551 B1
(45) Date of Patent: Jul. 24, 2001

(54) CATHETER CALIBRATION AND USAGE MONITORING SYSTEM

(75) Inventors: Daniel Osadchy, Haifa; Shlomo Fried, Zichron Yaacov; Shlomo Ben-Haim, Haifa; Maier Fenster, Petach Tikva, all of (IL)

(73) Assignee: Biosense, Inc., New Brunswick, NJ (US)

( * ) Notice: Subject to any disclaimer, the term of this patent is extended or adjusted under 35 U.S.C. 154(b) by 0 days.

(21) Appl. No.: 09/117,840

(22) PCT Filed: Feb. 14, 1997

(86) PCT No.: PCT/IL97/00060

§ 371 Date: Feb. 17, 1999

§ 102(e) Date: Feb. 17, 1999

(87) PCT Pub. No.: WO97/29678

PCT Pub. Date: Aug. 21, 1997

Related U.S. Application Data

(60) Provisional application No. 60/011,723, filed on Feb. 15, 1996, and provisional application No. 60/017,635, filed on May 17, 1996.

(51) Int. Cl.[7] ............................................. A61B 5/05
(52) U.S. Cl. ................................................ 600/424
(58) Field of Search .................................. 600/424, 300, 600/407; 128/898, 899; 341/50, 65, 78

(56) References Cited

U.S. PATENT DOCUMENTS

| | | | |
|---|---|---|---|
| 3,644,825 | 2/1972 | Davis, Jr. et al. | 324/41 |
| 3,868,565 | 2/1975 | Kuipers | 324/34 R |
| 4,017,858 | 4/1977 | Kuipers | 343/100 R |
| 4,054,881 | 10/1977 | Raab | 343/112 R |
| 4,560,930 | 12/1985 | Kouno | 324/207 |
| 4,570,354 | 2/1986 | Hindes | 33/534 |

(List continued on next page.)

FOREIGN PATENT DOCUMENTS

| | | | |
|---|---|---|---|
| 0 650 694 A1 | 10/1994 | (EP) | A61B/5/05 |
| WO 93/15654 | 2/1993 | (WO) | A61B/5/027 |

(List continued on next page.)

OTHER PUBLICATIONS

"Effects of laser irradiation delivered by flexible fiberoptic system on the left ventricular internal myocardium" American Heart Journal, Sep. 1983, pp. 587–590.

Dorothy Bonn, "High–Power laser help the Ischaemic Heart", The Lancet, vol. 348 (Jul. 13, 1996) p. 118.

Mahmood Mirhoseini et al. "Transmyocardial Laser Revascularization: A Review" Journal of Clinical Laser & Medicine Surgery. vol. 11 (1993) pp. 15–19.

*Primary Examiner*—Marvin M. Lateef
*Assistant Examiner*—Eleni Mantis Mercader
(74) *Attorney, Agent, or Firm*—Louis J. Capezzuto

(57) ABSTRACT

A probe (20) for insertion into the body of a subject, the probe (20) having distal (22) and proximal ends, and including an electronic microcircuit (90), which stores information relating to calibration of the probe (20). Preferably, the microcircuit (90) stores a calibration code, which is encrypted. Alternatively or additionally, the microcircuit (90) stores a usage code, which controls availability of the probe (20) to a user thereof. Preferably, the probe (20) includes access control circuitry (90) that allows the usage code to be changed so as to reduce the availability of the probe (20), but not to increase the availability thereof.

21 Claims, 7 Drawing Sheets

U.S. PATENT DOCUMENTS

| | | | |
|---|---|---|---|
| 4,592,356 | 6/1986 | Gutierrez | 128/339 |
| 4,613,866 | 9/1986 | Blood | 343/448 |
| 4,642,786 | 2/1987 | Hansen | 364/559 |
| 4,651,436 | 3/1987 | Gaal | 33/533 |
| 4,710,708 | 12/1987 | Rorden et al. | 324/207 |
| 4,788,987 | 12/1988 | Nickel | 128/777 |
| 4,849,692 | 7/1989 | Blood | 324/208 |
| 4,869,238 | 9/1989 | Opie et al. | 128/6 |
| 4,905,698 | 3/1990 | Strohl, Jr. et al. | 128/653 R |
| 4,917,095 | 4/1990 | Fry et al. | 128/660.03 |
| 4,921,482 | 5/1990 | Hammerslag et al. | 604/95 |
| 4,931,059 | 6/1990 | Markham | 606/185 |
| 4,945,305 | 7/1990 | Blood | 324/207.117 |
| 5,002,137 | 3/1991 | Dickinson et al. | 175/19 |
| 5,042,486 | 8/1991 | Pfeiler et al. | 128/653 R |
| 5,059,197 | 10/1991 | Urie et al. | 604/164 |
| 5,078,144 | 1/1992 | Sekino et al. | 128/660.03 |
| 5,081,993 | 1/1992 | Kitney et al. | 128/661.08 |
| 5,099,845 | 3/1992 | Besz et al. | 128/653.1 |
| 5,125,924 | 6/1992 | Rudko | 606/12 |
| 5,125,926 | 6/1992 | Rudko et al. | 606/19 |
| 5,158,084 | 10/1992 | Ghiatas | 128/657 |
| 5,172,056 | 12/1992 | Voision | 324/207.17 |
| 5,195,540 | 3/1993 | Shiber | 128/898 |
| 5,195,968 | 3/1993 | Lundquist et al. | 604/95 |
| 5,197,482 | 3/1993 | Rank et al. | 128/749 |
| 5,211,165 | 5/1993 | Dumoulin et al. | 128/653.1 |
| 5,215,680 | 6/1993 | D'Arrigo | 252/307 |
| 5,217,484 | 6/1993 | Marks | 606/200 |
| 5,234,426 | 8/1993 | Rank et al. | 606/1 |
| 5,251,635 | 10/1993 | Dumoulin et al. | 128/653.1 |
| 5,253,647 | 10/1993 | Takahashi et al. | 128/653.1 |
| 5,255,680 | 10/1993 | Darrow et al. | 128/653.1 |
| 5,265,610 | 11/1993 | Darrow et al. | 128/653.1 |
| 5,267,960 | 12/1993 | Hayman et al. | 604/106 |
| 5,273,025 | 12/1993 | Sakiyama et al. | 128/6 |
| 5,275,166 | 1/1994 | Vaitekunas et al. | 128/660.03 |
| 5,295,484 | 3/1994 | Marcus et al. | 128/660 |
| 5,295,486 | 3/1994 | Wollschager et al. | 128/661.01 |
| 5,301,682 | 4/1994 | Debbas | 128/737 |
| 5,309,913 | 5/1994 | Kormos et al. | 128/653 |
| 5,325,873 | 7/1994 | Hirschi et al. | 128/899 |
| 5,368,564 | 11/1994 | Savage | 604/95 |
| 5,368,592 | 11/1994 | Stern et al. | 606/33 |
| 5,373,849 | 12/1994 | Maroney et al. | 128/662 |
| 5,375,596 | 12/1994 | Twiss et al. | 128/653.1 |
| 5,377,678 | 1/1995 | Dumoulin et al. | 128/653.1 |
| 5,380,316 | 1/1995 | Aita et al. | 606/7 |
| 5,383,454 | 1/1995 | Bucholz | 128/653.1 |
| 5,383,874 | 1/1995 | Jackson et al. | 606/1 |
| 5,383,923 | 1/1995 | Webster, Jr. | 607/125 |
| 5,385,148 | 1/1995 | Lesh et al. | 128/662.06 |
| 5,389,096 | 2/1995 | Aita et al. | 606/15 |
| 5,391,199 | 2/1995 | Ben Haim | 607/122 |
| 5,403,356 | 4/1995 | Hill et al. | 607/14 |
| 5,404,297 | 4/1995 | Birk et al. | 362/421 |
| 5,409,004 | 4/1995 | Sloan | 128/657 |
| 5,423,321 | 6/1995 | Fontenot | 128/664 |
| 5,425,367 | 6/1995 | Shapiro et al. | 128/653 |
| 5,425,382 | 6/1995 | Golden et al. | 182/899 |
| 5,429,132 | 7/1995 | Guy et al. | 128/653.1 |
| 5,431,168 | 7/1995 | Webster, Jr. | 128/658 |
| 5,433,198 | 7/1995 | Desai | 128/642 |
| 5,437,277 | 8/1995 | Dumoulin et al. | 128/653.1 |
| 5,443,489 | 8/1995 | Ben-Haim | 607/115 |
| 5,450,846 | 9/1995 | Goldreyer | 128/642 |
| 5,465,717 | 11/1995 | Imran et al. | 128/642 |
| 5,471,982 | 12/1995 | Edwards et al. | 128/642 |
| 5,471,988 | 12/1995 | Fujio et al. | 128/660.03 |
| 5,480,422 | 1/1996 | Ben-Haim | 607/122 |
| 5,483,951 | 1/1996 | Frassica et al. | 600/104 |
| 5,487,391 | 1/1996 | Panescu | 128/699 |
| 5,538,008 | 7/1996 | Crowe | 128/751 |
| 5,554,152 | 9/1996 | Aita et al. | 606/7 |
| 5,555,883 | 9/1996 | Avitall | 128/642 |
| 5,558,091 | 9/1996 | Acker et al. | 128/653.1 |
| 5,558,092 | 9/1996 | Unger et al. | 128/660.03 |
| 5,577,502 | 11/1996 | Darrow et al. | 128/653.1 |
| 5,588,432 | 12/1996 | Crowley | 128/660.03 |
| 5,617,857 | 4/1997 | Chader et al. | 128/653.1 |
| 5,622,169 | 4/1997 | Golden et al. | 128/653.1 |
| 5,715,822 | 2/1998 | Watkins et al. | 128/653.5 |
| 5,724,264 * | 3/1998 | Rosenberg et al. | 364/559 |
| 5,729,129 | 3/1998 | Acker | 324/207.12 |
| 5,742,718 * | 4/1998 | Harman et al. | 385/88 |
| 5,897,498 * | 4/1999 | Canfield et al. | 600/437 |

FOREIGN PATENT DOCUMENTS

| | | |
|---|---|---|
| WO 94/00050 | 1/1994 | (WO) . |
| WO 94/04938 | 3/1994 | (WO) . |
| WO 94/06349 | 3/1994 | (WO) . |
| WO 94/23647 | 10/1994 | (WO) . |
| WO 94/28782 | 12/1994 | (WO) . |
| WO 95/05773 | 3/1995 | (WO) . |
| WO 95/07657 | 3/1995 | (WO) . |
| WO 95/09562 | 4/1995 | (WO) . |
| WO 95/10226 | 4/1995 | (WO) . |
| WO 95/19738 | 7/1995 | (WO) . |
| WO 96/05768 | 2/1996 | (WO) . |
| WO 96/41119 | 12/1996 | (WO) . |
| WO 97/03609 | 2/1997 | (WO) . |
| WO 97/29678 | 8/1997 | (WO) . |
| WO 97/29679 | 8/1997 | (WO) . |
| WO 97/29683 | 8/1997 | (WO) . |
| WO 97/29684 | 8/1997 | (WO) . |
| WO 97/29685 | 8/1997 | (WO) . |
| WO 97/29701 | 8/1997 | (WO) . |
| WO 97/29709 | 8/1997 | (WO) . |
| WO 97/29710 | 8/1997 | (WO) . |
| WO 97/29803 | 8/1997 | (WO) . |
| WO 97/32179 | 9/1997 | (WO) . |

* cited by examiner

CATHETER CALIBRATION AND USAGE MONITORING SYSTEM

RELATED APPLICATIONS

This application claims the benefit of U.S. Provisional patent applications No. 60/011,723, titled "Catheter Calibration System", filed Feb. 15, 1996 and No. 60/017,635, titled "Catheter Calibration System", filed May 17, 1996, the disclosures of both of which incorporated herein by reference. This application is also related to a PCT application titled "Medical Procedures and Apparatus Using Intrabody probes", filed on even date by applicant Biosense Inc., in the U.S. receiving office and designating, inter alia, the U.S.

FIELD OF THE INVENTION

The present invention relates generally to systems for medical diagnosis and treatment, and specifically to medical catheters whose location can be detected.

BACKGROUND OF THE INVENTION

Various methods and devices have been described for determining the position of a probe or catheter tip inside the body using electromagnetic fields, such as in U.S. Pat. No. 5,042,486 and PCT patent publication No. WO 94/0938, whose disclosures are incorporated herein by reference. Other electromagnetic tracking systems, not necessarily for medical applications, are described in U.S. Pat. Nos. 3,644, 825, 3,868,565, 4,017,858, 4,054,881 and 4,849,692, whose disclosures are likewise incorporated herein by reference.

U.S. Pat. No. 5,391,199, filed Jul. 20, 1993, which is assigned to the assignee of the present patent application and whose disclosure is incorporated herein by reference, describes a system that incorporates a catheter, which includes a position measuring device that can determine the position of the catheter in three dimensions, but not its orientation.

PCT patent application No. PCT/US95/01103, which is likewise assigned to the assignee of the present patent application and whose disclosure is incorporated herein by reference, describes a catheter system including means for determining the six-dimensions of position and orientation of the catheter's distal tip. This system uses a plurality of non-concentric coils adjacent to a locatable site in the catheter, for example near its distal tip. Preferably three orthogonal coils are used. These coils generate signals in response to externally applied magnetic fields, which allow for the computation of six position and orientation coordinates, so that the position and orientation of the catheter are known without the need for imaging the catheter.

U.S. Pat. No. 5,383,874 (Jackson et al.) describes a system for identifying and monitoring catheters, including identification means carried within the handle of the catheter body. In one embodiment of the invention of this patent, the handle includes a solid-state microchip pre-programmed with a digital value representing the catheter's identification code and other operational and functional characteristics of the catheter. The handle is connected by a cable to a control console, which reads data from the microchip. In one disclosed embodiment, the microchip may record the number of times the catheter has been used. Digital data storage in the catheter handle adds multiple digital signal wires to the catheter.

SUMMARY OF THE INVENTION

The coils of the '103 patent application and other systems for electromagnetic detection of catheter position and orientation are generally located in the catheter at a small distance proximal to the catheter's distal tip, since the distal tip is typically occupied by an electrode or other functional element. Therefore, the position and orientation detection system must be calibrated to take into account the displacement of the distal tip of the catheter relative to the location of the coils. Because of manufacturing variations, this displacement generally varies from one catheter to another.

Furthermore, the coils used to generate position signals may not be precisely orthogonal. For purposes of computing the position and orientation of the catheter, the axes of the coils define the respective axes of a coordinate system that is fixed to the catheter tip, and the directions of these axes must be known relative to the catheter. If these axes deviate from orthogonality, the respective degrees of deviation must be known and corrected for in the position and orientation computation.

Additionally, the relative gains of the coils determine the strengths of the respective position signals that the coils generate in response to externally-applied fields. Since these signal strengths are used in computing the position and orientation of the catheter, deviations of the gains from their expected values will lead to inaccuracy in the computed position and orientation. Therefore, the respective gains of the coils must be known and corrected for in the position and orientation computation.

It would, therefore, be desirable to pre-calibrate the catheter, preferably at the time of manufacture, so as to measure and compensate for variations in the positions, orientations and gains of coils used to generate position signals.

Preferably the calibration data should be recorded in such a way as to alleviate the need for recalibration and manual entry of calibration data before each use.

It is, therefore, an object of the present invention to provide a method of calibrating a device that is used to determine the position and orientation of a catheter, wherein the calibration information is retained in the catheter.

A further object of the present invention is to provide means for convenient electronic storage and recall of calibration information regarding a catheter.

In one aspect of the present invention, this calibration information is stored digitally in a microcircuit whose location is easily accessible to signal processing circuits and computing apparatus, so that the catheter need not contain digital signal wires, and digital electronic signals transmitted from the microcircuit to the signal processing circuits and computing apparatus do not interfere with low-level analog signals conveyed by wires from the distal end of the catheter to the circuits.

In preferred embodiments of the present invention, a device used to determine the position and orientation of a catheter inside the body comprises a plurality of coils adjacent to the distal end of the catheter. The catheter further comprises an electronic microcircuit adjacent to the proximal end of the catheter, which microcircuit stores information relating to the calibration of the device.

Preferably the microcircuit comprises a read/write memory component, such as an EEPROM, EPROM, PROM, Flash ROM or non-volatile RAM, and the information is stored in digital form.

In preferred embodiments of the present invention, this calibration information includes data relating to the relative displacement of the distal tip of the catheter from the coils. In some other preferred embodiments of the present invention, the calibration information also includes data relating to deviation of the coils from orthogonality, or data relating to the respective gains of the coils, or a combination of these data.

In some preferred embodiments of the present invention, in which the catheter is electrically isolated from signal processing and computing apparatus, the calibration information includes data relating to isolation circuitry in the catheter. Preferably, the catheter is isolated by at least one inductive element, such as an isolation transformer, adjacent to the proximal end of the catheter or in a handle associated with the catheter. Alternatively, the catheter may be isolated by one or more opto-isolaters, or other types of isolation circuitry known in the art. Such inductive elements and other isolation circuitry typically introduce non-linearities in signals conveyed thereby. Such non-linearities may lead to significant distortions particularly in analog signals conveyed by wires from the distal end of the catheter to the signal processing circuits. Therefore, the calibration information preferably includes data relating to signal non-linearities introduced by the inductive elements and/or other isolation circuitry.

In a preferred embodiment of the invention, the catheter is a wireless catheter which is not physically connected to the signal processing and/or computing apparatus. Rather, a transmitter/receiver is attached to a proximal end of the catheter. The transmitter/receiver communicates with the signal processing and/or computer apparatus using wireless communication methods, such as IR (infra red), RF or acoustic transmissions. One benefit of this type of configuration is that the catheter, which is inserted into the (electrically sensitive) heart can easily be made electrically floating. Another benefit is a reduction in the amount of cabling and wiring which in which one of the many operators might get entangled and/or accidentally pull out of the body. Still another advantage is the ease of sterilizing and maintaining the sterility of such a catheter, since the entire catheter may be sterilized as a single unit. In a preferred embodiment of the invention, the proximal end of the catheter, which includes the transmitter/receiver, is attached to an operator's belt. Preferably, there is a handle disposed on the catheter, a few feet away from the proximal end thereof, for control of the catheter. As can be appreciated, when such a catheter is used for ablation or for infusion of materials into the body, it is preferably momentarily connected to an external device, such as an RF generator.

In preferred embodiments of the present invention, the microcircuit is contained in a connector at the proximal end of the catheter. Preferably this connector couples electronic signals from the catheter to signal processing circuits and computing apparatus.

In preferred embodiments of the present invention, electronic signals coupled by the connector comprise both digital and analog signals. Furthermore, in some preferred embodiments of the present invention, the analog signals include both electrophysiological signals received by electrodes in the catheter and position and orientation signals generated by the coils. Preferably the position and orientation signals are conveyed by twisted wire pairs or shielded wires, and the connector also includes shielding to reduce noise and interference in these signals.

In other preferred embodiments of the present invention, the catheter includes one or more analog-to-digital (A/D) converter circuits, which convert electrophysiological signals and position and orientation signals from analog to digital form. In these embodiments, the connector couples only digital signals from the catheter to the signal processing circuits and computing apparatus. In one such preferred embodiment, an A/D converter is adjacent to the distal tip of the catheter. In other such preferred embodiments, an A/D converter is adjacent to the proximal end of the catheter, for example, in a handle attached to the catheter or in the connector.

Preferred embodiments of the present invention further provide a method of calibrating a device used to detect the position and orientation of the distal tip of a catheter, wherein the calibration information is stored in the catheter. Prior to operation of the device, a computer reads the stored calibration information and uses this information in determining the position and orientation of the catheter inside the body.

In preferred embodiments of the present invention in which the device used to determine position and orientation comprises coils adjacent to the distal end of the catheter, calibration information regarding the respective gains and orientations of the coils is generated by placing the distal end of the catheter in a known, predetermined position and orientation and applying to it known magnetic fields. The coils generate signals in response to the magnetic fields, which signals are detected and compared to normal signal values in order to calculate calibration data. These calibration data are then used to correct subsequent position and orientation determinations, so as to account for the deviation of the gains and orientations of the coils from normal values.

Furthermore, in preferred embodiments of the present invention, calibration information regarding the displacement of the distal tip of the catheter relative to the coils is generated by placing the distal tip of the catheter in one or more predetermined positions and orientations and applying known magnetic fields to the catheter. The signals generated by the coils in response to the magnetic fields are detected and used to calculate a correction function, which may be used subsequently in the determination of the position and orientation of the distal tip of the catheter.

In preferred embodiments of the present invention, a mechanical jig holds the catheter in one or more predetermined positions and orientations during calibration, and radiators generate known, substantially uniform magnetic fields in the vicinity of this jig. Signals generated by the coils are analyzed and used to produce calibration data regarding the gains of the coils and deviations of the coils from orthogonality.

In other preferred embodiments of the present invention, a mechanical jig holds the catheter in a plurality of predetermined positions and orientations during calibration. Radiators generate predetermined, non-uniform magnetic fields in the vicinity of this jig, wherein the magnetic field strengths and directions are known as functions of position in the jig. Signals generated by the coils are analyzed and used to produce calibration data regarding the respective displacements of the coils relative to the tip of the catheter.

In some preferred embodiments of the present invention, apparatus for use in calibrating the device for detecting the catheter's position and orientation includes a heater and temperature sensor, which maintain the catheter's distal tip at a predetermined, known temperature during calibration. Preferably, the tip is maintained at the temperature of the body into which the catheter is to be inserted, for example 37° C. In this way, temperature-related errors in calibration, for example, due to temperature-related changes in the inductance of the coils in the catheter, may be avoided.

The calibration data that are produced in accordance with any of the above preferred embodiments may be recorded in the form of lookup tables, polynomial coefficients or other forms known in the art, which are then stored in a microcircuit in the catheter.

In preferred embodiments of the present invention, calibration data are produced and recorded at the time of manufacture, and the microcircuit is configured so as to prevent subsequent recording of calibration data by a user. In some such preferred embodiments of the present invention, the microcircuit comprises an EPROM or PROM device, which is contained in a connector at the proximal end of a catheter, and the input and output connections of the EPROM or PROM are coupled to pins of the connector. Calibration data are recorded in the EPROM or PROM at the time of manufacture using a suitable programming device, which receives data from a computer used in calibration. The EPROM or PROM programming device is connected to the catheter connector and programs the EPROM or PROM by inputting digital signals thereto through the connector. Thereafter, the EPROM or PROM may not be re-programmed.

In other such preferred embodiments of the present invention, wherein the microcircuit comprises an EEPROM or non-volatile RAM device, the EEPROM or non-volatile RAM device includes a write-enable input connection, of a type known in the art, which is connected to a write-enable pin in a connector at the proximal end of a catheter. At the time of calibration, the write-enable input is enabled, and calibration data are recorded in the microcircuit. Thereafter the write-enable input is disabled, for example by removing the write-enable pin or by connecting it to electrical ground, so that further calibration data may not be recorded in the microcircuit.

Alternatively, in preferred embodiments of the present invention wherein the microcircuit comprises an EEPROM device, the write-enable input may be disabled by sending a write-protect command to the device. This command may be reversible or irreversible.

In still other preferred embodiments of the present invention, the microcircuit comprises access control circuitry, such as, for example, the X76F041 Password Access Security Supervisor (PASS™) SecureFlash ROM device, manufactured by Xicor, Inc. The microcircuit is preferably programmed with a password, so that after calibration data are produced and recorded at the time of manufacture, further calibration data may not be recorded in the microcircuit, with the possible exception of data recording by factory-authorized personnel to whom the password is known.

In some preferred embodiments of the present invention, data recorded in the microcircuit include a calibration code, which is encrypted in accordance with methods known in the art, so as to ensure that calibration data have not been altered or corrupted. When a user connects the catheter to a suitable console, which console comprises a computer, the computer reads the calibration code and compares the code with pre-programmed values. If the code does not match the desired pre-programmed value, the computer causes a message to be displayed indicating that the catheter may not be appropriately calibrated. The computer may prevent further operation until a catheter having a code matching the desired pre-programmed value is connected thereto.

Preferably the calibration code is encrypted using a method that prevents decryption by unauthorized parties, for example the RSA encryption scheme, using a public key and a private key, or other methods known in the art. When a method such as RSA encryption is used, the private key is known only to authorized manufacturers of the catheter, so as to prevent the possible use of unauthorized substitutes of possibly inferior quality.

In further preferred embodiments of the present invention, data recorded in the microcircuit include an expiration date and time, after which the catheter may not be used. When a user connects the catheter to a suitable console, which console comprises a computer, the computer reads the expiration date and time and compares then to the actual date and time, generated, for example, by a real-time clock circuit. If the expiration date and time have passed, the computer causes a message to be displayed indicating that the catheter is unsuitable for further use. The computer may prevent further operation until a catheter having a valid expiration date and time is connected thereto.

Preferably the expiration date and time are recorded by the console computer by programming the microcircuit in the catheter when the catheter is first used. Thus, when the catheter is connected to a console for the first time, the computer detects that no expiration date and time have yet been recorded in the microcircuit, and programs the microcircuit with the appropriate expiration data and time, at a pre-set interval after the actual date and time. The pre-set interval is preferably determined by the manufacturer, based on the expected useful life of the catheter.

In a preferred embodiment in which the microcircuit comprises access control circuitry, the microcircuit is programmed so that a memory location therein is operable in a "read access and program only" mode. The mode may be changed only by entry of an appropriate password, which is generally not available to users of the system. In the "read access and program only" mode, a number stored in the memory location may be decreased, by changing a bit from "1" to "0", but not increased, since the microcircuit as programmed will not permit a "0" to be changed to a "1". Preferably the memory location is set at the time of manufacture to contain a maximum value, i.e., all bits set to "1". Then, as described above, at the time of first use, the computer programs the microcircuit with the appropriate expiration time and date by changing one or more bits in the register from "1" to "0". Thereafter, the expiration date cannot be changed to any later date (unless the correct password is first entered).

Alternatively or additionally, the microcircuit comprising access control circuitry, as described above, may be used to track the number of times the catheter has been used and/or the duration of use, in a manner that is protected from possible tampering or error by a user thereof. Preferably, a record corresponding to the number of times and/or the length of time that the catheter may be used is stored in a memory location in the device at the time of manufacture, and the microcircuit is programmed so that this memory location is operable in the "read access and program only" mode, as described above. Each time the catheter is used, and/or at regular time intervals during use, the computer reads the record in the memory location and reduces it by changing one or more bits therein from "1" to "0". When the record stored in the memory location reaches zero, or some other predetermined minimum value, the computer causes a message to be displayed to the user indicating that the catheter is unsuitable for further use and, preferably, prevents further operation until a suitable catheter is connected thereto.

There is therefore provided in accordance with a preferred embodiment of the present invention, a probe for insertion into the body of a subject, the probe having distal and proximal ends, and including an electronic microcircuit, which stores information relating to calibration of the probe. Preferably the microcircuit stores a calibration code, which is encrypted.

Preferably, the microcircuit stores a usage code, which controls availability of the probe to a user thereof, and the probe includes access control circuitry that allows the usage code to be changed so as to reduce the availability of the probe, but not to increase the availability thereof. The microcircuit preferably stores the usage code in a memory location therein that is controlled by the access circuitry so as to operate in a read access and program only mode, which mode may be changed by entry of a password to the access control circuitry. Preferably, the usage code includes date information. Preferably, the probe includes a device that generates signals responsive to the position or orientation of the probe, and the information relating to calibration of the probe includes information relating to calibration of the signal generating device. Preferably, this device is adjacent to the distal end of the probe.

Preferably, the signal generating device includes one or more coils, and the information relating to calibration includes information relating to a gain of at least one of the one or more coils. Furthermore, the information relating to calibration preferably includes information relating to an angular orientation of at least one of the one or more coils, and additionally, information relating to a positional displacement of the signal generating device, relative to the distal end of the probe.

In preferred embodiments of the present invention in which the probe includes isolation circuitry, the information relating to calibration preferably includes information relating to a non-linearity of the isolation circuitry. Preferably, the microcircuit is adjacent to the proximal end of the probe. Moreover, the probe preferably includes a connector at its proximal end, in which the microcircuit is contained.

Additionally, the microcircuit is preferably a programmable memory device, which may comprise an EEPROM, non-volatile RAM, EPROM, Flash ROM or PROM device.

There is further provided in accordance with a preferred embodiment of the present invention, apparatus for determining the position of a probe in the body of a subject, including a probe as described above; and a console, including a computer, which receives position- or orientation-responsive signals from the probe and the information relating to calibration of the probe, and uses them to determine the position of the probe.

Preferably, the microcircuit is adjacent to the proximal end of the probe. Moreover, the probe preferably further includes a connector at its proximal end, in which the microcircuit is contained in the connector, and the console further includes a mating receptacle, which is adapted to be coupled with the probe connector.

Preferably, the microcircuit is a programmable memory device, and the probe includes one or more connections adapted for programming the programmable memory device, which may be an EEPROM, non-volatile RAM, EPROM, Flash ROM or PROM device. Additionally, the mating receptacle preferably includes means for disabling at least one of the connections for programming the programmable memory device.

Preferably, the computer is further adapted to program the programmable memory device. In preferred embodiments of the present invention in which the memory device is an EPROM or PROM device, the console preferably further includes EPROM or PROM programming apparatus, which is adapted to program the EPROM or PROM device.

There is further provided in accordance with a preferred embodiment of the present invention, a method of calibrating a probe for insertion into the body of a subject, including determining calibration data relating to the probe, and programming a microcircuit in the probe so as to record the calibration data in the microcircuit.

Preferably, the method also includes encrypting a calibration code and programming the microcircuit with the encrypted code. The method preferably further includes reading the encrypted calibration code and notifying a user of the probe, or ceasing operating of the probe, if the encrypted code does not match a predetermined code.

Preferably, programming the microcircuit includes setting a usage record, which is indicative of a first or final use date of the probe and/or of the number of times the probe may be re-used and/or of the remaining duration of time during which the probe may be used. Preferably, when the probe is used the usage record is updated. Preferably, programming the microcircuit includes restricting access to the usage flag, preferably by setting a password, so that the usage record may thereafter be changed so as to reduce availability of the probe to the user. but not to increase the availability. Preferably, the calibration data relate to a signal generating device, which generates signals responsive to the position or orientation of the probe. Preferably, the signal generating device has a gain, and the calibration data include data relating to the gain of the device. Alternatively or additionally, the calibration data may include data relating to an angular orientation of the signal generating device and data relating to a positional displacement of the position- or orientation-responsive signal generating device, relative to the probe.

There is also provided in accordance with a preferred embodiment of the present invention, a method of determining the position or orientation of a probe, including determining calibration data relating to the probe and programming a microcircuit in the probe, in accordance with the preferred embodiments described above; and computing the position or orientation of the probe inside the body based on the position- or orientation-responsive signals and on the calibration data.

There is also provided in accordance with a preferred embodiment of the invention, a method of controlling a usage of a probe having an encrypted code stored therein, including reading the encrypted code and notifying a user of the probe if the encrypted code does not match a predetermined code.

There is further provided in accordance with a preferred embodiment of the invention a method of controlling a usage of a probe having an encrypted code stored therein, including reading the encrypted code and ceasing operating of the probe if the encrypted code does not match a predetermined code. Alternatively, the code is compared to a range of values. Preferably, the method includes updating the usage record on the probe.

There is also provided in accordance with a preferred embodiment of the invention a method of calibrating a probe for insertion into the body of a subject, including providing a probe having a locatable portion and a signal generating device, which device generates signals responsive to the position or orientation of the probe, fixedly coupling said signal generating device and said locatable portion in one or more predetermined positions and orientations, applying predetermined magnetic fields to the probe, which magnetic fields are known at the vicinity of the signal generating device and which magnetic fields cause the signal generating device to generate the position- or orientation-responsive signals and receiving signals generated by the signal generating device.

Preferably, at least some of the calibration data are determined by applying substantially uniform magnetic fields to the probe. Alternatively or additionally, at least some of the calibration data are determined by applying spatially variable magnetic fields to the probe. Alternatively or additionally the position- or orientation-responsive signals generated by the signal generating device have an amplitude, which is characterized by a proportionality to a directional component of the magnetic fields applied thereto, and the calibration data include data relating to said proportionality.

Alternatively or additionally, the calibration data include data relating to an angular orientation of the position- or orientation-responsive signal generating device. Alternatively or additionally, the calibration data include data relating to a positional displacement of the position- or orientation-responsive signal generating device, relative to the probe.

In a preferred embodiment of the invention, the method includes heating the probe, preferably, to approximately 37° C.

In a preferred embodiment of the invention, the calibration data is stored on the probe.

There is also provided in accordance with a preferred embodiment of the invention, apparatus for calibration of a probe having a position sensing device therein, including a plurality of coils, wherein the coils define three substantially orthogonal axes and a central region, and are adapted to generate substantially uniform magnetic fields along the directions of the three axes in the central region, and means for fixing the distal end of the probe in the central region. Preferably, the coils include three orthogonal pairs of mutually parallel coils. Alternatively or additionally, the apparatus includes a clamp for holding the probe in a fixed position and orientation in the central region.

There is further provided in accordance with a preferred embodiment of the invention, apparatus for calibration of a probe, having a position sensing device therein, including a jig, including a plurality of receptacles adapted for insertion of the probe thereinto, each said receptacles defining a different predetermined position and orientation of the probe and a plurality of coils, wherein the coils generate magnetic fields that are different for the different predetermined positions and orientations.

In a preferred embodiment of the invention, the apparatus includes a heater, which heats the probe. Preferably, the Apparatus includes a temperature sensor, which senses the temperature of the probe.

There is also provided in accordance with a preferred embodiment of the invention a wireless catheter including an elongate flexible body having a distal end and a proximal end, a signal generating portion at the distal end of the body and a transmitter which transmits signals generated by the signal generation portion to an external receiver. Preferably, the transmitter includes a receiver, which receives transmissions from an external transmitter. Preferably, the above apparatus is adapted for calibrating the probe in accordance with the methods described above.

The present invention will be more fully understood from the following detailed description of the preferred embodiments thereof, taken together with the drawings in which:

DETAILED DESCRIPTION OF PREFERRED EMBODIMENTS

Figure 1:
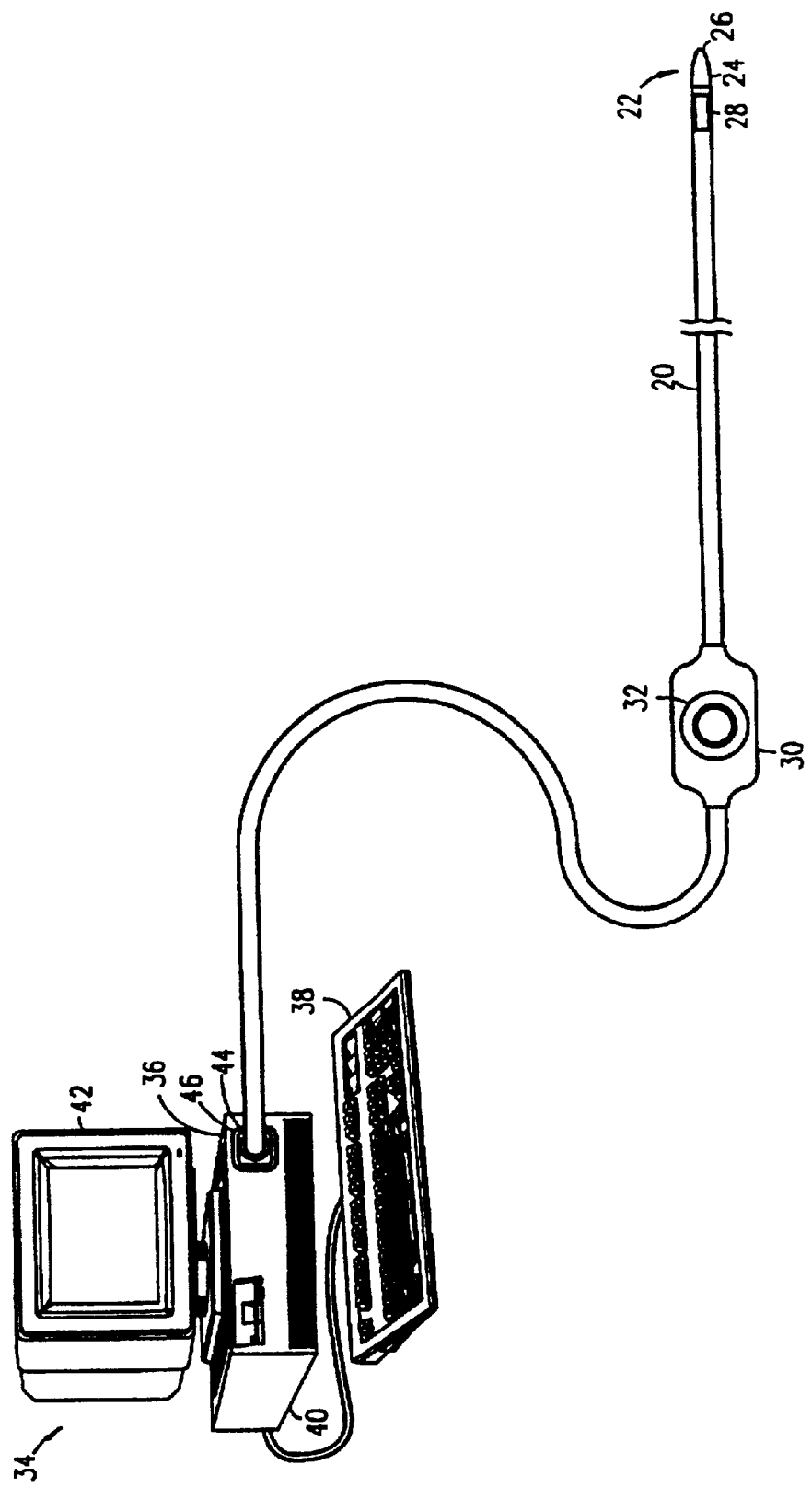
FIG. 1 is a perspective view of a system including a catheter in accordance with a preferred embodiment of the present invention.

FIG. 1 shows a catheter system in accordance with a preferred embodiment of the present invention. The system comprises an elongate probe, preferably a catheter 20, for insertion into the human body. It will be understood that although the following preferred embodiments are described with reference to a catheter, the present invention is equally applicable to other types of probes.

The distal end 22 of catheter 20 includes a functional portion 24 for performing diagnostic and/or therapeutic functions, adjacent to distal tip 26. Functional portion 24 may, for example, comprise electrodes (not shown in the figure) for performing electrophysiological measurements or for electrosurgical ablation of areas of pathology in the heart. Alternatively or additionally, the functional portion may comprise other types of sensors, or optical or ultrasound imaging devices.

Distal end 22 of catheter 20 further includes a device 28 that generates signals used to determine the position and orientation of the catheter within the body. Device 28 is preferably adjacent to functional portion 24. There is preferably a fixed positional and orientational relationship between device 28 and portion 24, at least during the calibration process.

Catheter 20 preferably includes a handle 30 for operation of the catheter by a surgeon, wherein controls 32 on handle 30 enable the surgeon to steer the distal end of the catheter in a desired direction, or to position and/or orient it as desired.

The system shown in FIG. 1 further comprises a console 34, which enables the user to observe and regulate the functions of catheter 20. Console 34 preferably includes a computer 36, keyboard 38, signal processing circuits 40, which are typically inside the computer, and display 42. Signal processing circuits 40 typically receive, amplify, filter and digitize signals from catheter 20, including signals generated by position signal generating device 28, whereupon these digitized signals are received and used by computer 36 to compute the position and orientation of the catheter.

Catheter 20 is coupled at its proximal end by connector 44 to a mating receptacle 46 on console 34. Preferably, catheter 20 further contains one or more isolation transformers (not shown in the figures), which electrically isolate the distal portion of the catheter from console 34. The isolation transformers are preferably contained in catheter handle 30.

Figure 2:
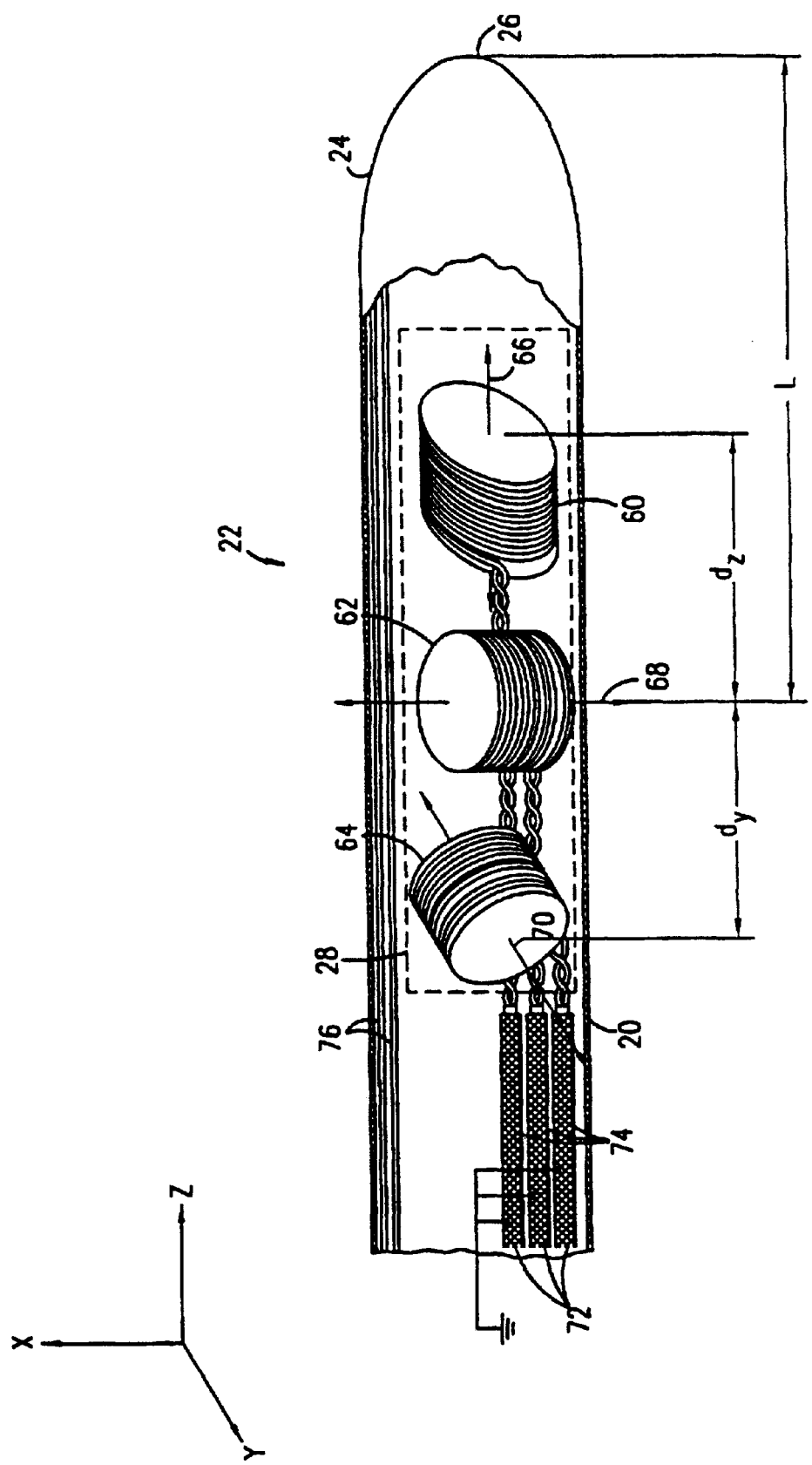
FIG. 2 is a detailed sectional view of the distal end of the catheter of FIG. 1.

Reference is now made to FIG. 2, which shows a detailed view of distal end 22 of catheter 20 in accordance with a preferred embodiment of the present invention. Device 28 comprises three non-concentric coils 60, 62 and 64, such as described in PCT patent application No. PCT/US95/01103, now published as WO96/05768, whose disclosure is incorporated herein by reference. This device enables continuous generation of six dimensions of position and orientation information. Coils 60, 62 and 64 have respective axes 66, 68 and 70 which preferably define orthogonal Cartesian axes Z, X and Y, respectively, as shown in FIG. 2, wherein the Z-axis is parallel to the long axis of catheter 20 and the X- and Y-axes define a plane perpendicular thereto. The coils each have a fixed position and orientation with respect to each other.

Although preferred embodiments of the present invention are described here with reference to the position signal generating device shown in FIG. 2 and described above, it will be understood that the inventive concepts of the present invention are similarly applicable to probes including other position sensing devices. For example, preferred embodiments of the present invention may comprise a single coil for generating position signals, or two or more such coils, which may be concentric or non-concentric. Other preferred embodiments of the present invention may comprise other types of position sensing devices, such as Hall effect devices.

As shown in FIG. 2, device 28 is located in catheter 20 at a distance L from distal tip 26, where L is here defined for convenience as the distance along the Z-axis from the central axis 68 of coil 62 to tip 26. Respective axes 66 and 70 of coils 60 and 64 are displaced from axis 68 by respective distances dy and $d_z$.

When a time-varying external magnetic field is applied to distal end 22 of catheter 20, coils 60, 62 and 64 generate analog signals, which are preferably conveyed through the catheter by coil wires 72. The amplitudes of these analog signals are typically small relative to other electrical signals in and around catheter 20, such as the electrophysiological signals measured by functional portion 24 and conveyed through the catheter by functional wires 76. Furthermore, external magnetic fields may also cause undesired electrical currents, not generated by coils 60, 62 and 64, to flow in coil wires 72. These other electrical signals and undesired electrical currents can cause noise or interfering signals to appear together with the signals generated by the coils. Therefore, in preferred embodiments of the present invention, wires 72 are configured as twisted pairs and may also be shielded from electromagnetic interference by shields 74, so as to maintain a high signal-to-noise ratio in the position and orientation signals received from the coils.

In an alternative preferred embodiment of the present invention, not shown in the figures, catheter 20 further includes one or more analog-to-digital (A/D) converters proximate to coils 60, 62 and 64, which convert the analog signals generated by the coils to digital form. In this embodiment, the coil signals are conveyed through the catheter in digital form. Signals measured by functional portion 24 may similarly be digitized. Thus, fewer wires are necessary to transport the signals and less of the catheter is taken up by signal wires.

As described in the 01103 PCT patent application, signal processing circuits 40 in console 34 receive the signals carried by coil wires 72 and convey them to computer 36, which computes the three-dimensional translational position of device 28 and the rotational orientation of axes 66, 68 and 70, relative to a fixed, external coordinate frame. The actual position and orientation of distal tip 26 are then computed by taking into account the distance L of tip 26 from the center of device 28, as defined by axis 68, and the orientation of axes 66, 68 and 70.

It has been found empirically that due to deviations in the process of manufacturing catheter 20, the distance L typically varies from one catheter to another, leading to errors in calculating the position of tip 26. Furthermore, axis 66 of coil 60 typically deviates from absolute alignment with the long axis of catheter 20, which passes through tip 26, and axes 66 and 70 of coils 60 and 64 respectively are typically not precisely orthogonal to axis 66 or to each other, thereby inducing additional errors in determination of position and orientation of the catheter. Finally, variations in the respective gains of coils 60, 62 and 64 and in the distances dy and $d_z$ may cause additional errors in determination of position and orientation of the catheter.

Therefore, in preferred embodiments of the present invention, the device 28 that is used to determine the position and orientation of catheter 20 is calibrated before the catheter is inserted into a patient's body. Preferably this calibration is performed using one or more jigs, such as those shown, for example, in FIGS. 3A, 3B and 4.

Figure 3A:
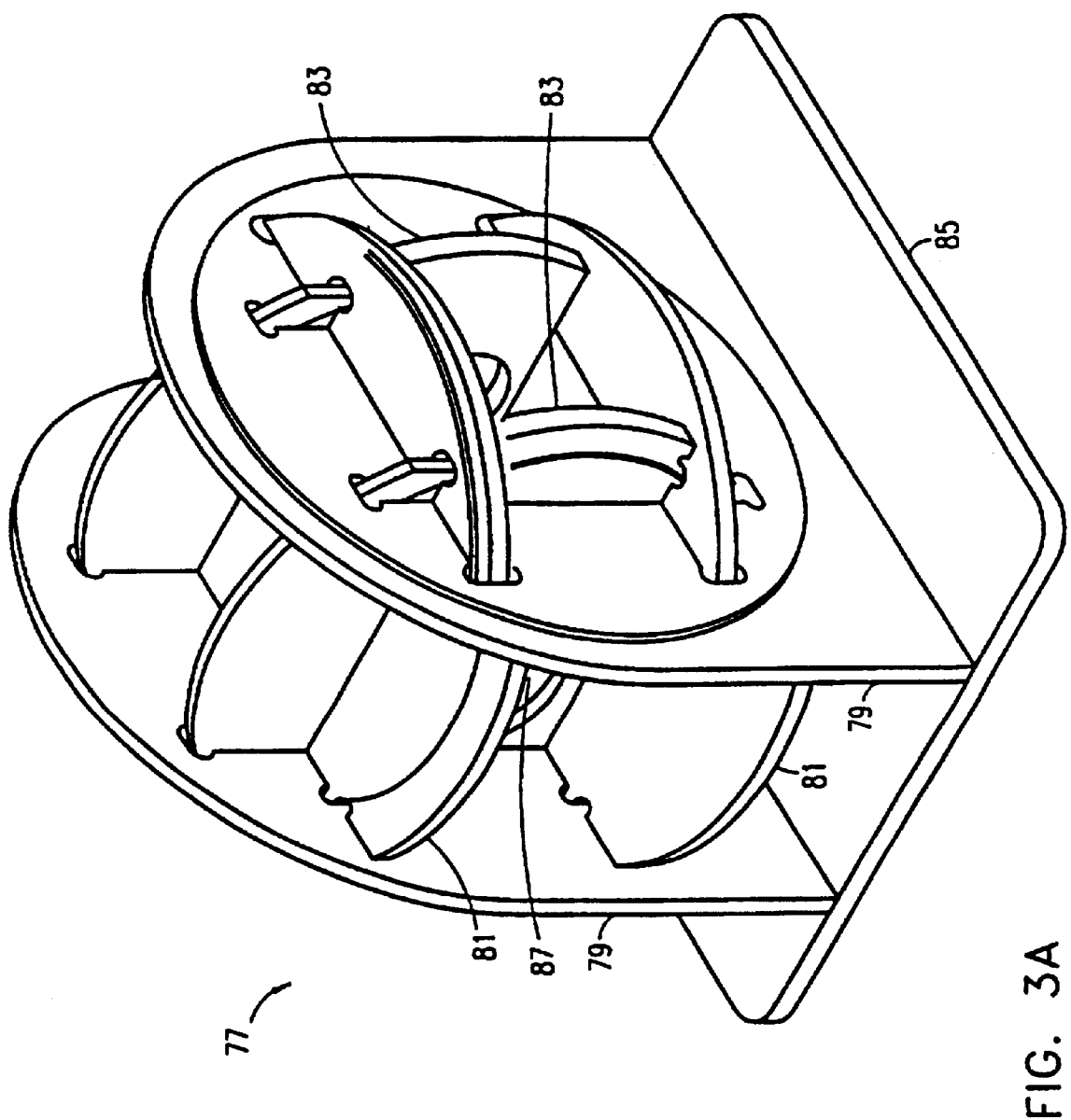
FIG. 3A is a perspective view of a jig useful in calibrating a catheter in accordance with a preferred embodiment of the present invention.
Figure 3B:
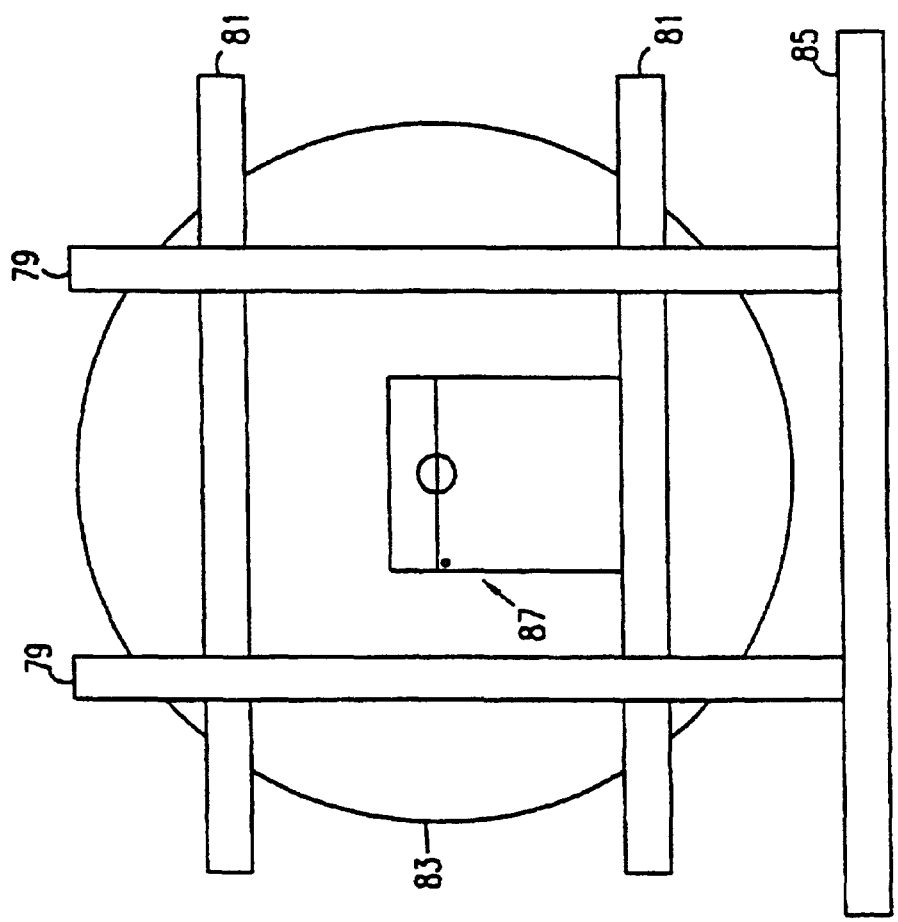
FIG. 3B is a schematic side view of the jig of FIG. 3A.

FIGS. 3A and 3B show a preferred embodiment of a jig 77 for use in calibrating the respective gains and deviations from orthogonality of coils 60, 62 and 64. Jig 77 comprises three mutually orthogonal pairs of parallel radiator coils 79, 81 and 83, mounted on base 85. The radiator coils are coupled to radiator driver circuitry, not shown in the figures, which causes the radiator coils to generate magnetic fields. Each radiator coil pair generates a magnetic field that is substantially normal to the planes defined by the pair of coils, and is thus substantially orthogonal to fields generated by the other two radiator coil pairs.

The radiator coils are configured so as to generate predetermined, substantially uniform magnetic fields in a region adjacent to the center of the jig, i.e., in a region centrally located in between the three pairs of radiator coils. Preferably the driver circuitry is adjusted so that the amplitudes of the respective magnetic fields generated by three radiator coil pairs are equal.

Figure 3C:
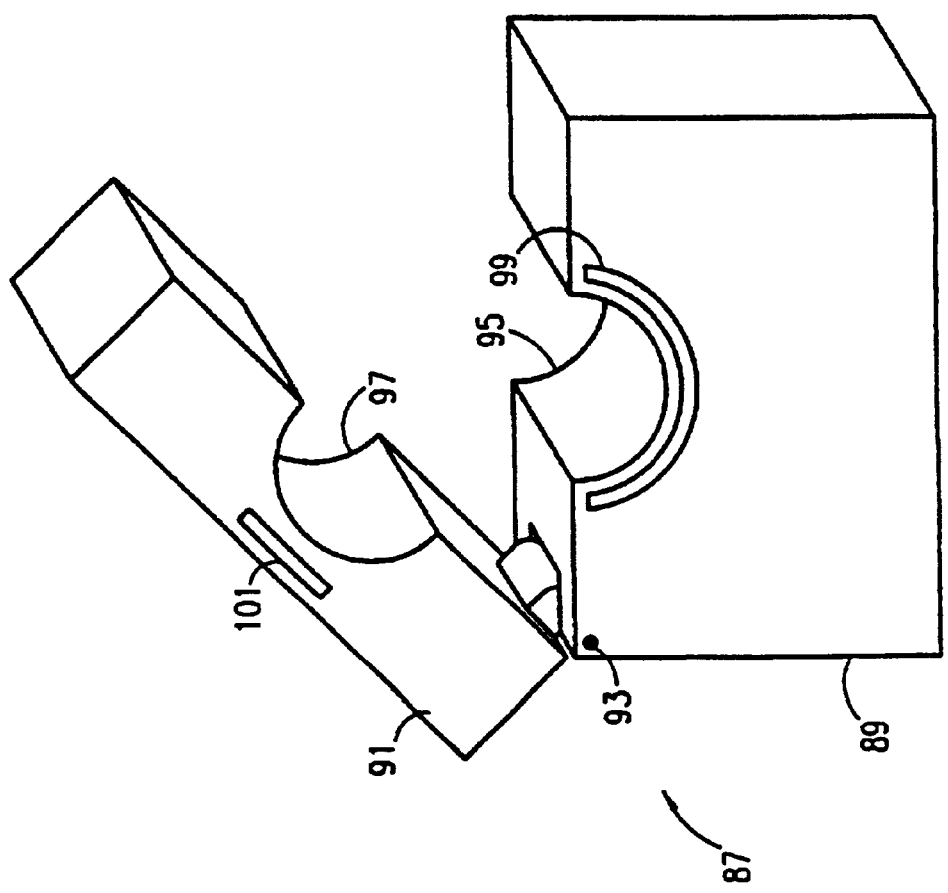
FIG. 3C is a perspective view of a catheter clamp for use in conjunction with the jig of FIG. 3A.

As shown in FIG. 3B, jig 77 further comprises a catheter clamp assembly 87, which is located inside the jig and not seen in FIG. 3A. As shown in FIG. 3C, clamp assembly 87 includes a clamp base 89, which is fixed to one or more of radiator coils 79, 81 and 83 in a known position and orientation. Preferably clamp assembly 87 is constructed and configured in jig 77 so that a catheter held in the clamp assembly will be in the region of substantially uniform magnetic fields adjacent to the center of the jig, and so that the long axis of the catheter will be substantially normal to the planes defined by one of the pairs of parallel radiator coils, for example, coils 83 as shown in FIG. 3B. A clamp cover 91 is rotatably attached to base 89 by a hinge 93. Base 89 and cover 91 include respective semi-circular grooves 95 and 97, whose radii are substantially equal to the radius of catheter 20.

Clamp assembly 89 preferably includes a heating element 99 and at least one temperature sensor 101, which are used to heat distal end 22 of catheter 20 to a temperature substantially equal to the temperature of the body into which the catheter is to be inserted, and to maintain the distal end at that temperature during calibration. As is known in the art, the response of coils 60, 62 and 64 to magnetic fields may change as a function of temperature. For example, when the coils are wound around ferrite cores, their inductance may change with temperature, which change can introduce errors into the calibration of device 28. Therefore, distal end 22 is typically heated to and maintained at a temperature of 37° C. during calibration, although other temperatures may be chosen, for example when catheter 20 is to be used under conditions of hypothermia, such as are generally induced during open-heart surgery.

To use jig 77 in calibrating catheter 20, the catheter is inserted in groove 95, and rotated about its long axis to a desired rotational orientation, wherein preferably the X, Y and Z catheter axes shown in FIG. 2 are substantially aligned with the magnetic field directions defined by radiator coil pairs 83, 79 and 81, respectively. The desired rotational orientation may be indicated, for example, by fiducial marks or other features (not shown in the figures) on the catheter's outer surface. Alternatively, in preferred embodiments of the present invention in which catheter 20 is rotationally symmetrical about its long axis, the rotational orientation is unimportant, and there is no need to align the X and Y axes.

After catheter 20 has been inserted and aligned, as necessary, in groove 95, cover 91 is then lowered to hold the catheter in place. In this manner the catheter is fixed in a known orientation relative to the magnetic fields generated by radiator coils 81, 83 and 85.

The respective gains and angular orientations of catheter coils 60, 62 and 64 are then calibrated by sequentially activating radiator coil pairs 79, 81 and 83 to generate predetermined, known magnetic fields, and measuring the amplitudes of the signals generated by the catheter coils.

First, to calibrate the gains of the coils, total amplitudes of the respective catheter coil signals are derived by summing the squares of the amplitudes of the signals generated by each of catheter coils 60, 62 and 64 in response to each of the coil pairs in turn. Since the magnetic fields in the vicinity of coils 60, 62 and 64 have equal and substantially uniform components along each of the coil axes 66, 68 and 70, the total signal amplitudes will be independent of the respective orientations and positions of coils 60, 62 and 64, and will depend only on the respective coil gains. Thus, the measured total signal amplitudes may be used to determine respective normalization factors for coils 60, 62 and 64, by dividing the measured amplitudes by expected standard values. Subsequently the amplitudes of signals received from these coils may be multiplied by the respective normalization factors in order to correct for gain variations.

Jig 77 is further used to calibrate the respective angular orientations of coils 60, 62 and 64 relative to catheter 20, so as to correct for deviations from orthogonality. The normalized amplitude of the signal generated by each of coils 60, 62 and 64 in response to each of the magnetic fields will be proportional to the cosine of the angle between the respective coil axis 66, 68 or 70, and the direction of the applied magnetic field. Three such angle cosines, corresponding to the directions of the tree orthogonal magnetic fields applied by radiator coil pairs 79, 81 and 83, may thus be derived for each of catheter coils 60, 62 and 64. Since as noted above, catheter 20 is held in clamp assembly 87 is such a manner that the X, Y and Z catheter axes are substantially aligned with the three orthogonal magnetic field directions, the orientations of the coils relative to the catheter axes may thus be determined.

In preferred embodiments of the present invention, when the Z-axis magnetic field is activated, corresponding in this case to radiator coil pair 83, a normalized amplitude of the signal received from coil 60, $S_{60}(Z)$, is received and measured. The X- and Y-axis fields are similarly activated, and corresponding normalized signals $S_{60}(X)$ and $S_{60}(Y)$ are received. $S_{60}(X)$, $S_{60}(Y)$ and $S_{60}(Z)$ are used to calculate coil angle calibration factors for coil 60, which are thereafter recorded in catheter 20 and used in determining the catheter's position and orientation. A similar procedure is used to calibrate coils 62 and 64.

Although the magnetic fields generated by coil pairs 79, 81 and 83 are substantially orthogonal and of equal amplitudes, imprecise winding of the coil pairs may cause small deviations from orthogonality and equality. These deviations, if not corrected for, may cause errors in the calibration of catheter 20. Therefore, in preferred embodiments of the present invention, a master coil (not shown in the figures) is used to calibrate jig 77. Preferably this master coil is wound precisely, with a known, predetermined geometrical configuration and dimensions, so that its sensitivity to an applied magnetic field may be accurately calculated, using theoretical methods known in the art.

The master coil is placed in the center of jig 77 in a known, predetermined position and orientation, wherein the axis of the master coil is substantially parallel to the direction of the magnetic field generated by coil pair 79. This coil pair is activated, thereby causing the master coil to generate an electrical signal. This signal is recorded and compared with a standard signal value, in order to determine a calibration factor for coil pair 79. This procedure is repeated for coil pairs 81 and 83.

When catheter 20 is placed in jig 77 for calibration of the catheter, the signals received from coils 60, 62 and 64 are first corrected to account for the calibration factors of coil pairs 79, 81 and 83, before the gain normalization and angle calibration factors of the catheter are determined.

It will be appreciated that a single master coil may be used to calibrate multiple jigs, so that all of the calibrated jigs will give substantially identical results in calibrating catheters. Furthermore, the same master coil may also be used to calibrate radiator coils, which produce magnetic fields for detection of the position of catheter 20 inside the body of a subject, in accordance with the 01103 PCT patent application.

It will further be understood that a first master coil may be used to produce and calibrate additional master coils, to be used in turn to calibrate other jigs and radiator coils. After a jig is calibrated using the first master coil, a second master coil is similarly placed in the jig. Signals generated by the second master coil are measured, using the procedure described above for calibrating the jig. Differences between the signals generated by the second master coil, and those that were generated by the first master coil under the same conditions, are used to determine calibration factors for the second master coil. These calibration factors may be stored in the second master coil, using devices and methods similar to those used to store calibration factors in catheter 20, in accordance with preferred embodiments of the present invention.

Figure 4:
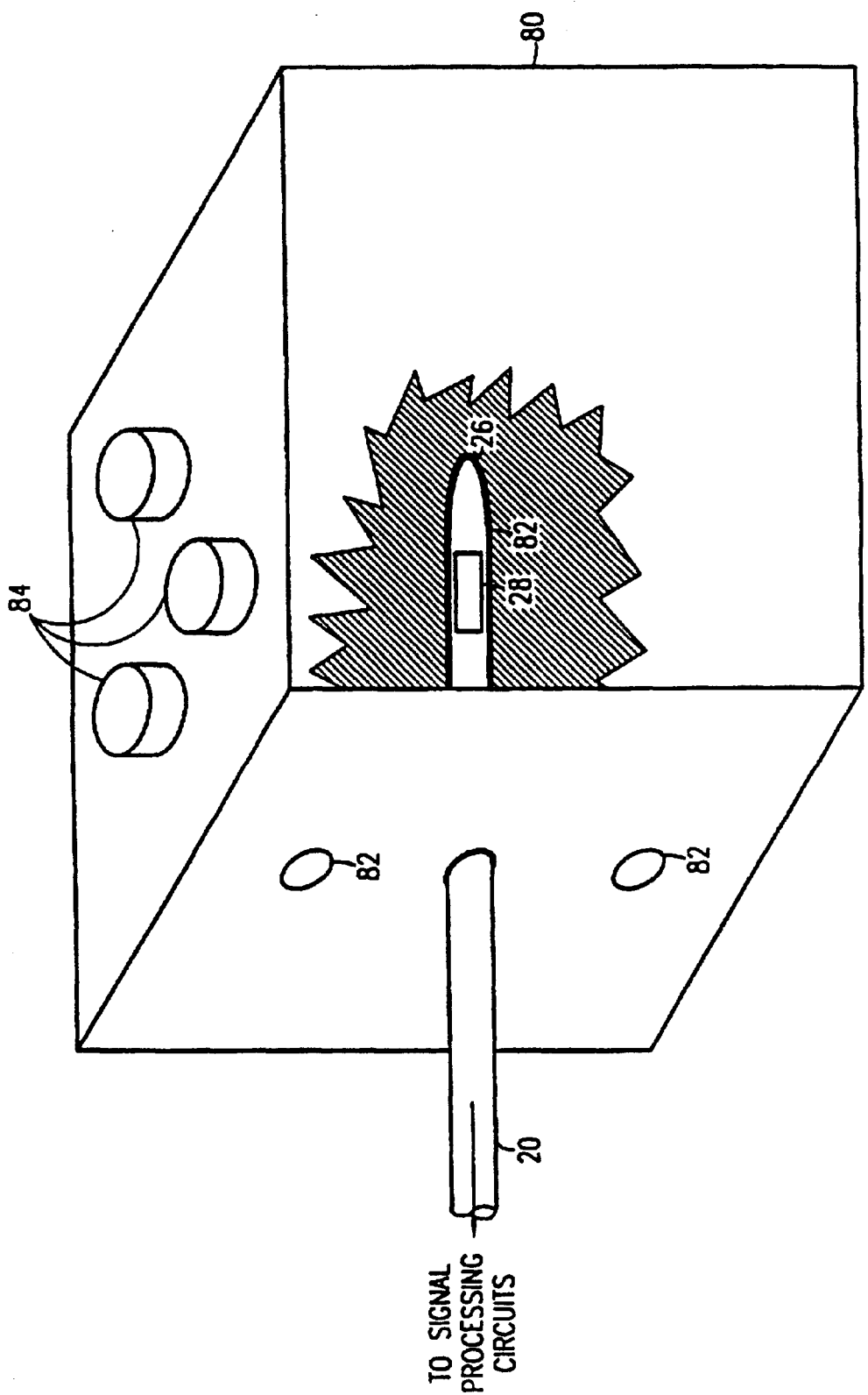
FIG. 4 is a partially cutaway perspective view of another calibration jig useful in calibrating a catheter in accordance with a preferred embodiment of the present invention.

FIG. 4 shows a preferred embodiment of a jig 80 useful in calibrating the displacements of coils 60, 62 and 64 relative to catheter tip 26. Jig 80 comprises one or more receptacles 82 into which catheter 20 may be inserted. Each of receptacles 82 has a known, predetermined depth and angular orientation relative to jig 80. When the catheter is fully inserted into a receptacle, distal tip 26 of the catheter abuts the inner end of the receptacle. Jig 80 and receptacles 82 are so constructed that the catheter fits snugly into the receptacles, so that when the catheter is fully inserted, the location and angular orientation of its distal tip are precisely determined with respect to a frame of reference defined by the jig. Preferably, jig 80 also includes a heating element and one or more temperature sensors (not shown in FIG. 4), as shown in FIG. 3C and described in reference thereto.

Preferred embodiments of jig 80 further comprise one or more radiator coils 84, which generate known, spatially varying magnetic fields, in the vicinity of device 28. These magnetic fields cause coils 60, 62 and 64 in device 28 to generate signals, which are conveyed through catheter 20 to signal processing circuits 40, and from these circuits to computer 36, as shown in FIG. 1. The computer measures the amplitudes of the respective signals generated by coils 60, 62 and 64, and then determines corrected values of the amplitudes using gain normalization and coil angle calibration factors, which have preferably been determined as described above. The corrected amplitudes are compared to expected standard values, based on the known magnetic field strength at the expected respective locations of the coils. Deviations between the corrected, measured amplitudes and the expected standard values are used to compute displacement correction factors, corresponding to deviations of the displacements L, $d_y$ and $d_z$, as shown in FIG. 2, from their respective expected values.

Calibration data regarding catheter 20 may be calculated in accordance with various methods known in the art. For example, in a preferred embodiment of the present invention, the gain normalization, angle calibration and displacement correction factors are stored electronically in the form of a look-up table, which is used by computer 36 to compute the position and orientation of the catheter's distal tip 26.

In an alternative preferred embodiment of the present invention of jig 80, the jig includes a plurality of receptacles, each in a different, predetermined position and orientation with respect to the frame of reference defined by the jig. Radiator coils 84 generate magnetic fields that are substantially identical to those generated by radiator coils (not shown in the figures) that are used to generate external magnetic fields for determining the position and orientation of catheter 20 inside the body of a subject. Moreover, radiator coils 84 are placed on jig 80 in relative positions and orientations that are substantially identical to the relative positions and orientations of the radiator coils that are used to generate external magnetic fields for determining the position and orientation of catheter 20 inside the body of a subject.

Catheter 20 is inserted into each of receptacles 82 in turn, and magnetic fields generated by radiators 84 cause coils 60, 62 and 64 in device 28 to generate signals, which are conveyed to signal processing circuits 40 and computer 36. The computer uses these signals to compute position data, in accordance with methods described in the 01103 PCT patent application, after first applying gain normalization and coil angle calibration factors, which have preferably been determined as described above. The computed position and orientation of device 28 are compared to the known, predetermined position and orientation of tip 26 in receptacle 82. The differences between the computed and known values of position and orientation are used to calculate an empirical displacement correction vector D, and an angle correction vector Θ. The values of D and Θ that are calculated for the plurality of positions and orientations defined by the plurality of receptacles 82 are used to generated a map of D and Θ as a function of measured position and orientation over the range of positions and orientations defined by jig 80. When catheter 20 is subsequently used inside a human body, computer 36 applies these correction vectors to the position and orientation signals generated by device 28, in order to determine the actual, correct position of tip 26.

Calibration vector functions D and Θ may be calculated and recorded in accordance with various methods known in the art. For example, in preferred embodiments of the present invention, polynomial functions of position coordinates x, y, z and angle coordinates $\theta_1$, $\theta_2$, $\theta_3$ are fit to the maps of D and Θ by methods known in the art, such as least-squares fitting. The polynomial coefficients thus derived are stored electronically and then applied by the computer in determining the correction vectors. Alternatively, the values of vector functions themselves are stored electronically in the form of look-up tables, which are used by computer 36 to compute the position and orientation of the catheter's distal tip 26.

In some preferred embodiments of the present invention, catheter 20 is electrically isolated from console 34 by isolation circuitry, for example by one or more isolation transformers in handle 30, as described earlier in reference to FIG. 1. Such inductive elements and other isolation circuitry typically introduce non-linearities in signals conveyed thereby, which may lead to distortion of the signals, particularly analog signals, conveyed to circuitry 40. These non-linearities are preferably measured at the time of catheter calibration, and the calibration information recorded in catheter 20 preferably then includes data relating to signal non-linearities introduced by isolation circuitry.

In preferred embodiments of the present invention, the calibration correction function that is determined in accordance with the methods described above or using other methods known in the art, is thereafter stored electronically in a memory device, which device is preferably in catheter 20. When the catheter is coupled to console 34, this memory device is accessible to the computer in the console.

Figure 5:
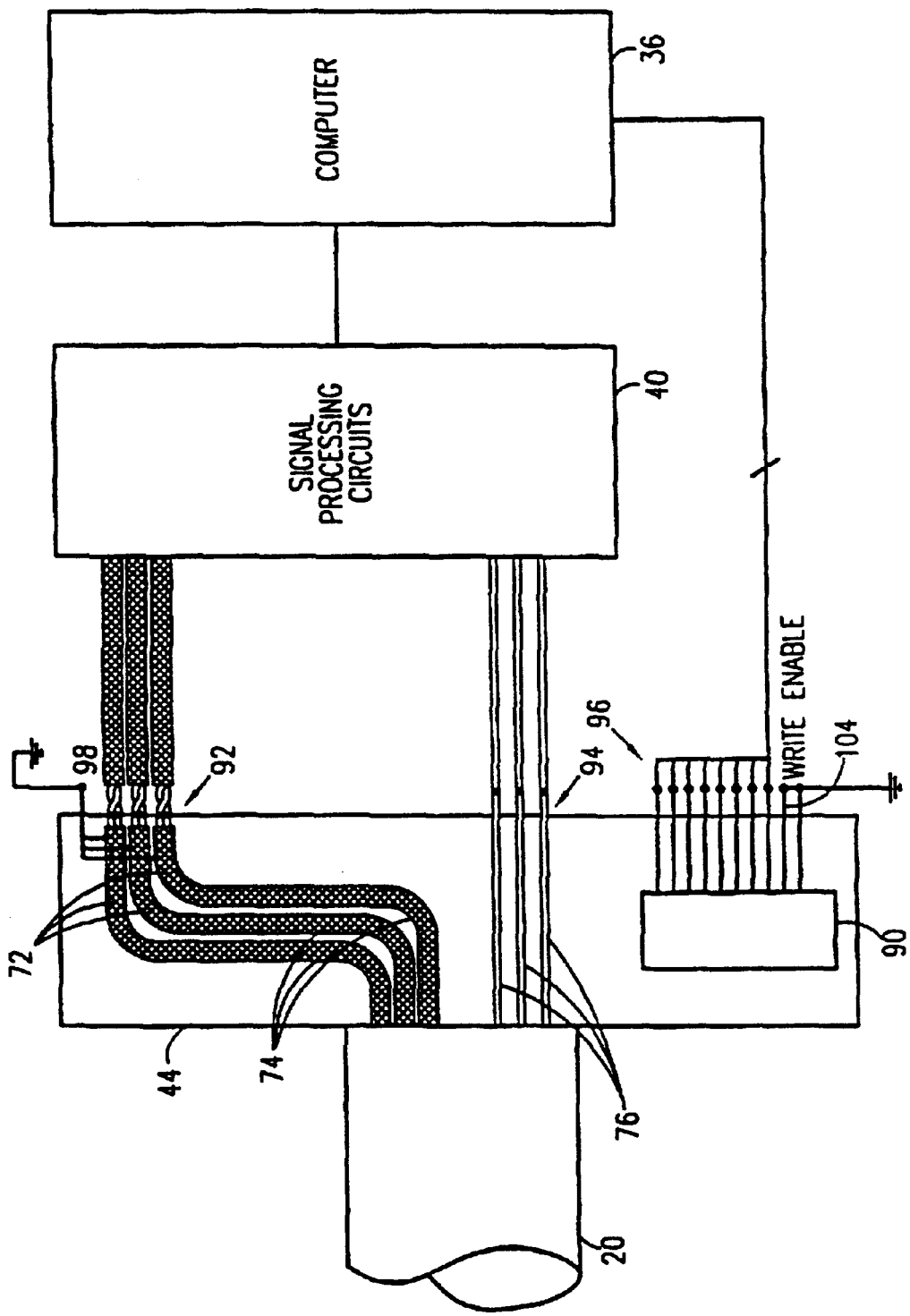
FIG. 5 is a detailed schematic view of a connector at the proximal end of a catheter in accordance with a preferred embodiment of the present invention.

In one such preferred embodiment of the present invention, illustrated schematically in FIG. 5, connector 44 includes a digital microcircuit 90 in which calibration correction function data for catheter 20 is electronically stored. Microcircuit 90 preferably includes an EEPROM or Flash ROM, but may alternatively include EPROM, PROM, non-volatile RAM, or other types of programmable memory devices known in the art. When a catheter 20 is calibrated, its specific correction data are stored in the microcircuit located in its console connector 44, which is conveniently accessible to the computer, as will be described below.

In the preferred embodiment shown in FIG. 5, connector 44 further includes pins 92, 94, 96 and 98, which mate with corresponding sockets in receptacle 46. Functional pins 94 couple analog electrophysiological signals conveyed over functional wires 76 to signal processing circuits 40. Coil pins 92 couple analog position and orientation signals conveyed by coil wires 72 from coils 60, 62 and 64 to signal processing circuits 40 and computer 36, which computes the position and orientation of catheter 20. The computer further reads the digital calibration correction function data stored in microcircuit 90 via memory pins 96, and uses these data to in computing the correct catheter position and orientation.

One or more write-enable pins 104 are likewise coupled to microcircuit 90. These pins are used to enable programming of the microcircuit with the desired calibration data. At the time of calibration, the write-enable input is enabled, and calibration data are recorded in the microcircuit. Thereafter the write-enable input is disabled, for example by removing the write-enable pin or by connecting it to electrical ground, as shown in FIG. 5, so that further calibration data may not be recorded in the microcircuit, and the microcircuit functions in a read-only mode.

Alternatively, in preferred embodiments of the present invention wherein microcircuit 90 comprises an EEPROM device, the write-enable input may be disabled by sending a write-protect command to the device. This command may be reversible or irreversible.

In other preferred embodiments of the present invention, microcircuit 90 comprises a device incorporating password-secured access control, and write-access to the microcircuit requires that an appropriate password first be entered. For example, in one such preferred embodiment, microcircuit 90 comprises a Password Access Security Supervisor (PASS™) X76F041 SecureFlash ROM device, manufactured by Xicor, Inc. The microcircuit is programmed with calibration data at the time of manufacture, and thereafter operates in a "read access only" mode, with all write operations locked out, or in a "read access and program only" mode, in which certain data, but not calibration data, may be written to the device, as will be described below. Changing the mode of operation of the microcircuit requires that an appropriate password be entered, which password is generally unavailable to users of the system.

In another preferred embodiment of the present invention, microcircuit 90 comprises an EPROM or PROM device, which is contained in the catheter connector, and the input and output connections of the EPROM or PROM are coupled to pins of the connector. Calibration data are recorded in the EPROM or PROM at the time of manufacture using a suitable programming device, not shown in the figures, which receives data from the computer used in calibration. The programming device is connected to catheter connector 44 and programs the EPROM or PROM by inputting digital signals thereto through the connector. Thereafter, the EPROM or PROM may not be re-programmed.

In some preferred embodiments of the present invention, data recorded in microcircuit 90 include a calibration code, which is encrypted in accordance with methods known in the art, so as to ensure that the calibration data have not been altered or corrupted. Preferably the calibration code includes a checksum. When the user connects catheter 20 to console 34, computer 36 reads the calibration code and compares the code with pre-programmed values. If the code does not match the desired pre-programmed value, the computer causes a message to be displayed by display 42 indicating that the catheter may not be appropriately calibrated. The computer may further cause the system to cease operation until a catheter having a code matching the desired pre-programmed value is connected thereto.

Preferably the calibration code is encrypted using a method that prevents decryption by unauthorized parties, for example the RSA encryption scheme, using a public key and a private key, or other methods known in the art. When a method such as RSA encryption is used, the private key is known only to authorized manufacturers of the catheter, so as to prevent the possible use of unauthorized substitutes of possibly inferior quality.

In further preferred embodiments of the present invention, data recorded in microcircuit 90 include an expiration date and time, after which the catheter may not be used. When a user connects catheter 20 to a console 34, computer 36 reads the expiration date and time and compares then to the actual date and time, generated, for example, by a real-time clock circuit. If the expiration date and time have passed, the computer causes a message to be displayed by display 42 indicating that the catheter is unsuitable for further use. The computer may prevent further operation until a catheter having a valid expiration date and time is connected thereto.

Preferably the expiration date and time arm recorded by computer 36 by programming microcircuit 90 in catheter 20 when the catheter is first used. Thus, when catheter 20 is connected to console 34 for the first time, computer 36 detects that no expiration date and time have yet been recorded in microcircuit 90, and programs the microcircuit with the appropriate expiration data and time, at a pre-set interval after the actual date and time. The pre-set interval is preferably determined by the manufacturer, based on the expected useful life of the catheter.

In preferred embodiments of the present invention in which microcircuit 90 comprises a device including access control circuitry, such as the aforementioned X76F041 device, the microcircuit is programmed so that a memory location therein is operable in a "read access and program only" mode. The mode may be changed only by entry of an appropriate password, which is generally not available to users of the system. In the "read access and program only" mode, a number stored in the memory location may be decreased, by changing a bit from "1" to "0", but not increased, since the microcircuit as programmed will not permit a "0" to be changed to a "1". Preferably the memory location is set at the time of manufacture to contain a maximum value, i.e., all bits set to "1". Then, as described above, at the time catheter 20 is first used, computer 36 programs the microcircuit with the appropriate expiration time and date by changing one or more bits in the register from "1" to "0". Thereafter, the expiration date cannot be changed to any later date (unless the correct password is first entered).

Alternatively or additionally, microcircuit 90 comprising access control circuitry, as described above, may be used to track the number of times catheter 20 has been used, in a manner that is protected from possible tampering or error by a user thereof. Preferably, a record corresponding to the number of times catheter 20 may be used is stored in a memory location in the device at the time of manufacture, and the microcircuit is programmed so that this memory location is operable in the "read access and program only" mode, as described above. Each time the catheter is used, computer 36 reads the record in the memory location and reduces it by changing one or more bits therein from "1" to "0". When all the bits in the record are equal to zero, or the record reaches some other predetermined minimum value, the computer causes a message to be displayed to the user indicating that the catheter is unsuitable for further use and, preferably, prevents further operation until a suitable catheter is connected thereto.

Similarly, either alternatively or additionally, microcircuit 90 may be used to track the duration of use of catheter 20. In this case, a record corresponding to the duration of use of the catheter is stored in a "read access and program only" memory location in the microcircuit. While the catheter is in use, at regular, predetermined intervals, computer 36 reads the record and reduces it by changing one or more bits therein from "1" to "0". When the entire record reaches zero, or some other minimum value, further operation is prevented, as described above. As noted earlier, the low-level analog signals conveyed from coils 60, 62 and 64 over coil wires 72 must generally be protected from interference due to other analog signals in functional wires 76 and digital signals conveyed to an from microcircuit 90. Therefore, in preferred embodiments of the present invention, as shown in FIG. 5, connector 44 includes electromagnetic shields 74, which are coupled to ground via pin 98 on the connector.

In another preferred embodiment of the present invention, shields 74 are active shields, which are driven by noise canceling circuitry (not shown).

It will further be appreciated that by locating microcircuit 90 in connector 44, the length of electrical conductors carrying digital signals in proximity to the low-level analog signals in coil wires 72 is held to a minimum, thereby reducing the possibility of electrical interference with the low-level signals.

In a preferred embodiment of the invention, catheter 20 is a wireless catheter which is not physically connected to the signal processing and/or computing apparatus. Rather, a transmitter/receiver is attached to a proximal end of the catheter and all electronic signals generated by the catheter are transmitted by the transmitter/receiver. The transmitter/receiver communicates with the signal processing and/or computer apparatus using wireless communication methods, such as IR (infra red), RF or acoustic transmissions. One benefit of this type of configuration is that the catheter, which is inserted into the (electrically sensitive) heart can easily be made electrically floating and/or completely isolated from any external (to the body) electrical power source. Another benefit is a reduction in the amount of cabling and wiring with which one of the many operators might get entangled and/or accidentally pull out of the body. Still another advantage is the ease of sterilizing and maintaining the sterility of such a catheter, since the entire catheter may be sterilized as a single unit. The power supply for such a catheter is preferably permanently enclosed within the catheter. When the catheter is used, the power supply is activated and it is capable of powering the catheter for a limited amount of time. Alternatively, the power supply is a rechargeable power supply which may be recharged after each use, thereby allowing multiple uses of the same catheter.

In a preferred embodiment of the invention, the proximal end of the catheter, which includes the transmitter/receiver, is attached to an operator's belt. Preferably, there is a handle disposed on the catheter, a few feet away from the proximal end thereof, for control of the catheter. As can be appreciated, when such a catheter is used for ablation or for infusion of materials into the body, it is preferably momentarily connected to an external device, such as an RF generator.

Although the above preferred embodiments have been described with reference to calibration of position and orientation sensing apparatus, in other preferred embodiments of the present invention, calibration data stored in catheter 20, and specifically in microcircuit 90, may relate to other aspects of the catheter. For example, in some preferred embodiments of the present invention, calibration data relating to a physiological sensor, actuator or therapeutic tool are stored in the catheter. In another preferred embodiment of the present invention, calibration data may be stored in the catheter regarding the gain of a piezoelectric motion control device used in steering the catheter's distal end.

It will be appreciated that the preferred embodiments of the invention described above are cited by way of example, and the full scope of the invention is limited only by the claims which follow.

What is claimed is:

1. A method of calibrating a probe for insertion into the body of a subject, comprising:

providing a probe having a programmable microcircuit and a distal end, the distal end including a functional portion adjacent to a distal tip of the distal end for performing diagnostic and/or therapeutic functions, the distal end also including a position signal generating device for generating signals used to determine the position of the probe within the subject's body;

determining calibration data for the position signal generating device with respect to the distal tip of the probe; and programming the microcircuit so as to record the calibration data in the microcircuit.

2. A method in accordance with claim 1, and comprising encrypting a calibration code and programming the microcircuit therewith.

3. A method in accordance with claim 2 comprising:

reading the encrypted code; and notifying a user of the probe if the encrypted code does not match a predetermined code.

4. A method in accordance with claim 3 comprising:

reading the encrypted code; and ceasing operating of the probe if the encrypted code does not match a predetermined code.

5. A method in accordance with claim 1, wherein programming the microcircuit includes setting a usage record.

6. A method in accordance with claim 5, wherein the usage record is indicative of a permitted use date of the probe.

7. A method in accordance with claim 5, wherein the usage record is indicative of how many times the probe may be re-used.

8. A method in accordance with claim 5, wherein the usage record is indicative of a duration of time during which the probe may be operated.

9. A method in accordance with claim 5, wherein programming the microcircuit includes restricting access to the usage record, so that availability of the probe to a user thereof may be reduced, but not increased.

10. A method in accordance with claim 9, wherein restricting access to the usage record comprises allowing one or more bits in the record to be changed from a first value to a second value thereof, but not from the second value to the first value.

11. A method in accordance with claim 1, wherein restricting access to the usage record comprises setting a password.

12. A method in accordance with claim 1, wherein the calibration data relate to the position signal generating device, which generates signals responsive to the position or orientation of the probe.

13. A method in accordance with claim 12, wherein the signal generating device has a gain, and the calibration data include data relating to the gain of the device.

14. A method in accordance with claim 12, wherein the calibration data include data relating to an angular orientation of the signal generating device.

15. A method in accordance with claim 12, wherein the calibration data include date relating to a positional displacement of the signal generating device, relative to the probe.

16. A method for programming a probe for insertion into the body of a subject, the method comprising the steps of:

providing a probe having a programmable microcircuit and a distal end, the distal end including a functional portion adjacent to a distal tip of the distal end for performing diagnostic and/or therapeutic functions, the distal end also including a position signal generating device for generating signals used to determine the position of the probe within the subject's body; and programming the microcircuit with an expiration date and time.

17. The method according to claim 16, including determining a pre-set interval for the expiration date and time based on the actual date and time when the probe is first used.

18. A method for programming and tracking usage of a probe for insertion into the body of a subject, the method comprising the steps of:

providing a probe having a programmable microcircuit and a distal end, the distal end including a functional portion adjacent to a distal tip of the distal end for performing diagnostic and/or therapeutic functions, the distal end also including a position signal generating device for generating signals used to determine the position of the probe within the subject's body;

programming the microcircuit with a number of times that the probe may be used; and tracking with the microcircuit the number of times that the probe is used.

19. The method according to claim 18, further comprising wherein the number of times defines a minimum value and preventing further operation of the probe upon reaching the minimum value.

20. The method according to claim 19, further comprising displaying a message to the user that the probe is unsuitable for further use upon reaching the minimum value.

21. A method for programming and tracking the usage of a probe for insertion into the body of a subject, the method comprising the steps of:

providing a probe having a programmable microcircuit and a distal end, the distal end including a functional portion adjacent to a distal tip of the distal end for performing diagnostic and/or therapeutic functions, the distal end also including a position signal generating device for generating signals used to determine the position of the probe within the subject's body;

storing a record in the microcircuit corresponding to a duration of use for the probe, the record including a minimum value;

reducing the record for each use of the probe; and preventing further operation of the probe when the record reaches the minimum value.

* * * * *

UNITED STATES PATENT AND TRADEMARK OFFICE
CERTIFICATE OF CORRECTION

| | | |
|---|---|---|
| PATENT NO. | : 6,266,551 B1 | Page 1 of 1 |
| DATED | : July 24, 2001 | |
| INVENTOR(S) | : Daniel Osadchy, Shlomo Fried, Shlomo Ben-Haim and Maier Fenster | |

It is certified that error appears in the above-identified patent and that said Letters Patent is hereby corrected as shown below:

<u>Column 20,</u>
Line 48, please delete "date" and insert -- data --

Signed and Sealed this

Fourth Day of June, 2002

*Attest:*

*Attesting Officer*

JAMES E. ROGAN
*Director of the United States Patent and Trademark Office*